United States Patent
Hao

(10) Patent No.: US 10,792,283 B2
(45) Date of Patent: Oct. 6, 2020

(54) QUINOLINE ANALOGS AS PHOSPHATIDYLINOSITOL 3-KINASE INHIBITORS

(71) Applicant: HANGZHOU ZHENGXIANG PHARMACEUTICALS CO., LTD., Hangzhou (CN)

(72) Inventor: Xiaolin Hao, Foster City, CA (US)

(73) Assignee: HANGZHOU ZHENGXIANG PHARMACEUTICALS CO., LTD., Hangzhou (CN)

( * ) Notice: Subject to any disclaimer, the term of this patent is extended or adjusted under 35 U.S.C. 154(b) by 166 days.

(21) Appl. No.: 16/072,150

(22) PCT Filed: Feb. 28, 2017

(86) PCT No.: PCT/US2017/019970
§ 371 (c)(1),
(2) Date: Jul. 23, 2018

(87) PCT Pub. No.: WO2017/155741
PCT Pub. Date: Sep. 14, 2017

(65) Prior Publication Data
US 2019/0365752 A1    Dec. 5, 2019

Related U.S. Application Data

(60) Provisional application No. 62/304,148, filed on Mar. 5, 2016.

(51) Int. Cl.
*A61K 31/506*    (2006.01)

(52) U.S. Cl.
CPC .................................. *A61K 31/506* (2013.01)

(58) Field of Classification Search
CPC ........................... C07D 401/12; C07D 401/14
See application file for complete search history.

(56) References Cited

U.S. PATENT DOCUMENTS

| | | | | |
|---|---|---|---|---|
| 2009/0137581 A1* | 5/2009 | Chen | ...... | A61P 19/02 514/234.2 |
| 2010/0331306 A1* | 12/2010 | Bui | ...... | A61P 7/00 514/210.21 |
| 2013/0267524 A1* | 10/2013 | Bui | ...... | A61P 7/06 514/249 |
| 2014/0343033 A1* | 11/2014 | Chang | ...... | A61P 11/00 514/210.16 |
| 2016/0016915 A1* | 1/2016 | Evarts | ...... | A61P 7/00 514/266.2 |

FOREIGN PATENT DOCUMENTS

| WO | WO 2008/118455 A1 | 10/2008 | |
| WO | WO 2012/037204 A1 | 3/2012 | |
| WO | WO 2012/061696 A1 | 5/2012 | |
| WO | WO 2013/152150 A1 | 10/2013 | |
| WO | WO-2015106014 A1 * | 7/2015 | ........ C07D 471/04 |
| WO | WO 2017/155741 A1 | 9/2017 | |

OTHER PUBLICATIONS

T. Cushing et al., 58 Journal of Medicinal Chemistry, 480-511 (2015) (Year: 2015).*

Cushing et al., "Discovery and in vivo evaluation of (S)-N-(1-(7-fluoro-2-(pyridin-2-yl)quinolin-3-yl)ethyl)-9H-purin-6-amine (AMG319) and related PI3Kδ inhibitors for inflammation and autoimmune disease," J Med Chem. Jan. 8, 2015;58(1):480-511.

International Search Report and Written Opinion dated Jun. 16, 2017, for International Application No. PCT/US2017/019970, 6 pages.

* cited by examiner

*Primary Examiner* — Mark L Shibuya
*Assistant Examiner* — Ebenezer O Sackey
(74) *Attorney, Agent, or Firm* — Cooley LLP

(57) ABSTRACT

The present disclosure provides selective phosphoinositide 3-kinase inhibitors of formula (A), or pharmaceutically acceptable salts thereof. These compounds are useful for the treatment of conditions mediated by one or more PI3K isoforms, such as PI3K delta (PI3Kδ). The present disclosure further provides methods of inhibiting phosphoinositide 3-kinase inhibitors using these compounds for treatment of disorders related to phosphatidylinositol 3-kinase activity.

20 Claims, No Drawings

QUINOLINE ANALOGS AS PHOSPHATIDYLINOSITOL 3-KINASE INHIBITORS

CROSS-REFERENCE TO RELATED APPLICATIONS

This application is the National Stage of International Application No. PCT/US2017/019970, filed Feb. 28, 2017, which claims the benefit of U.S. Provisional Application No. 62/304,148, filed on Mar. 5, 2016, the disclosures of which are hereby incorporated by reference in their entirety.

FIELD OF THE INVENTION

The present disclosure relates generally to quinoline analogs as inhibitors of phosphatidylinositol 3-kinase (PI3K) activity. More specifically, the invention further relates to the preparation of the disclosed PI3K inhibitor analogs and their use in pharmaceutical compositions for the treatment of various diseases, conditions and disorders related to PI3K activity.

BACKGROUND OF THE INVENTION

The class I phosphoinositide 3-kinases (PI3Ks) regulate phosphatidylinositol 4,5-bisphosphate (PIP2) phosphorylation. PI3K Converts PIP2 to the scaffolding binding element phosphatidylinositol (3,4,5)-trisphosphate (PIP3). PIP3 plays a key regulatory role in cell survival, signal transduction, control of membrane trafficking and other functions. (Di Paolo, G. et al. Nature 2006, 443, 651; Parker, P. J. et al. Biochem. Soc. Trans. 2004, 32, 893; Hawkins, P. T. et al. Biochem. Soc. Trans. 2006, 34, 647; Schaeffer, E. M. et al. Curr. Opin. Immnunol. 2000, 12, 282). Its dysregulation leads to various disease states such as cancer, inflammatory and auto-immune disorders.

The Class I PI3Ks consist of four kinases further delineated into 2 subclasses. Class 1A PI3Ks consist of three closely related kinases, PI3Kα, β, and δ existing as heterodimers composed of a catalytic subunit (p110α, β or δ) and one of several regulatory subunits. They generally respond to signaling through receptor tyrosine kinases (RTKs). PI3Kγ single class 1B isoform, responds mainly to G-protein coupled receptors (GPCRs), and is composed of a p110γ catalytic subunit and one of two distinct regulatory subunits. PI3Kα and PI3Kβ are ubiquitously expressed throughout a wide variety of tissue and organ types. PI3Kγ is found mainly in leukocytes, but also in skeletal muscle, liver, pancreas, and heart (Cantly, C. Science 2002, 1655). The expression pattern of PI3Kδ is restricted, to spleen, thymus, and peripheral blood leukocytes (Knight, Z. et al. Cell 2006, 125, 733).

PI3Kδ has been implicated as a major player in the adaptive immune system due to its expression pattern and evidence accumulated with genetically modified mice. Recently, activated PI3K delta syndrome (APDS) was described, a primary immunodeficiencies (PID) associated with a dominant gain-of-function mutation in which lysine replaced glutamic acid at residue 1021 (E1021K) in the p110δ protein. APDS was characterized by recurrent respiratory infections, progressive airway damage, and lymphopenia (Ivan Angulo et al. Science 2013, 342, 866). PI3Kδ inhibitors can potentially be supplemental to the treatments of B-cell related diseases such as rheumatoid arthritis (RA) and systemic lupus erythematosus (SLE) by the biologics rituximab (Rituxan) and belimumab (Benlysta), as well as primary immunodeficiencies (PID). Several PI3Kδ selective inhibitors, such as, idelalisib (GS-1101), IPI-145 and AMG 319 have entered the clinic targeting hematological malignancies, but few inhibitors have entered clinical trials for anti-inflammatory treatments (Cushing, T. et al. J Med Chem. 2015, 58, 480).

In July 2014, the FDA and EMA granted first-in class PI3K delta inhibitor idelalisib approval to treat different types of leukemia; its safety and effectiveness to treat relapsed FL and relapsed SLL were established in a clinical trial with patients with indolent non-Hodgkin lymphomas. ("FDA approves Zydelig for three types of blood cancers". Food and Drug Administration. Jul. 23, 2014). However, the U.S. label for idelalisib has a boxed warning describing toxicities that can be serious and fatal, including liver toxicity. Fatal and/or serious hepatotoxicity occurred in 18% of patients treated with idelalisib monotherapy and 11% of patients treated with idelalisib in combination trials. Elevations in ALT or AST are greater than 5 times the upper limit of what has occurred normally. The liver toxicity may be related to the inhibition and induction of CYP enzymes by idelalisib and its metabolite GS-563117. (http://www.accessdata.gov/drugsatfcla_docs/nda/2014/206545Orig1s000ClinPharmR.pdf).

More recently, it was reported that p110δ inactivation in mice protects against a broad range of cancers, including non-haematological solid tumors, and that p110δ inactivation in regulatory T cells unleashes CD8(+) cytotoxic T cells and induces tumor regression. Thus, p110δ inhibitors can break tumor-induced immune tolerance and potentially have wide usage in oncology. (Ali, et al., Nature: 2014, 510, 407-411). There still remains an unmet need for optimal PI3K delta inhibitors. For example, PI3K delta inhibitor can have improved in vivo stability to overcome the liability of inhibition or induction of CYP enzymes; an ideal PI3K delta inhibitor can have the potential of combination treatment of malignant tumors with other anti-cancer interventions, such as emerging immunotherapies. The present invention provides novel compounds that are inhibitors of PI3K isoforms with significantly improved profiles.

SUMMARY

Compounds and pharmaceutically acceptable salts, prodrug, or solvate thereof useful for inhibiting PI3K isoforms, such as PI3K delta, are described herein. Compositions, including pharmaceutical compositions that include the compounds are also provided, as are methods of using and making the compounds. The compounds provided herein may find use in treating diseases, disorders, or conditions that are mediated by PI3K isoforms, such as PI3K delta.

In one aspect, provided is a compound of formula (A), or a pharmaceutically acceptable salt, prodrug, or solvate wherein:

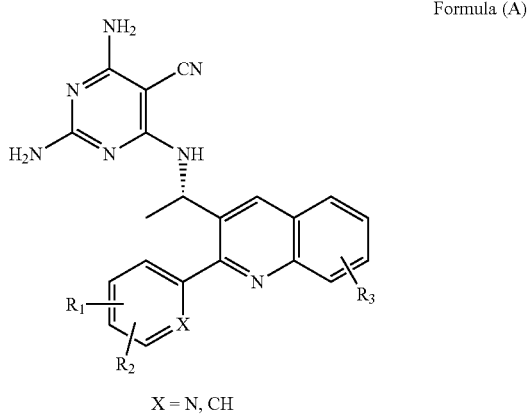

Formula (A)

X = N, CH

X is N or CH;

Each $R_1$ and $R_2$ is independently H, F, or $SO_2Me$.

$R_3$ is F or Cl.

In one embodiment of formula (A) where X is N, both $R_1$ and $R_2$ are H, $R_3$ is 7-F. The compound is of compound (2) in Table 1; or a pharmaceutically acceptable salt, prodrug, or solvate thereof.

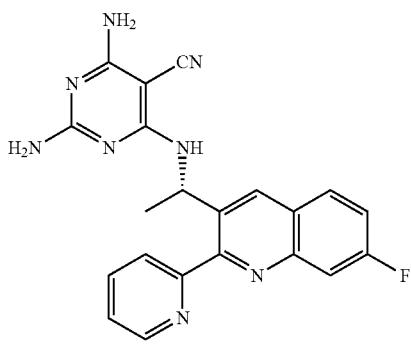

(2)

In another embodiment of formula (A) where X is C, $R_1$ is H, $R_2$ is 2-$SO_2Me$, $R_3$ is 8-F, the compound is compound (7) in Table 1, or a pharmaceutically acceptable salt, prodrug, or solvate thereof.

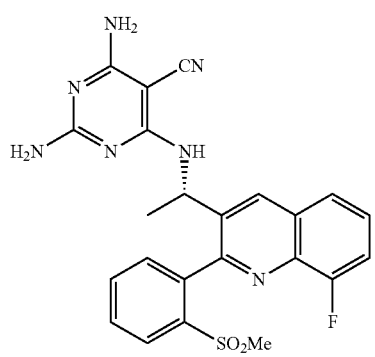

(7)

Also provided is a method of treating PI3K-mediated conditions or disorders with a compound of formula (A), or a pharmaceutically acceptable salt, prodrug, or solvate thereof. Further provided is a method of treatments of inflammatory diseases, such as asthma, chronic obstructive pulmonary disease, rheumatoid arthritis, multiple sclerosis, and lupus.

Also provided is a method of inhibiting the growth or proliferation of cancer cells comprising contacting the cancer cells with an effective amount of a compound of formula (A), or a pharmaceutically acceptable salt, prodrug, or solvate. Also provided is a method for increasing sensitivity of cancer cells to chemotherapy, comprising administering to a patient undergoing chemotherapy with a chemotherapeutic agent and a compound of formula (A), or a pharmaceutically acceptable salt, prodrug, or solvate, sufficient to increase the sensitivity of cancer cells to the chemotherapeutic agent.

Also provided are articles of manufacture that include a compound of formula (A), or a pharmaceutically acceptable, or prodrug, or solvate thereof.

DETAILED DESCRIPTION

It is intended and understood that each and every variation of $R_1$ and $R_2$ may be combined with each and every variation of X as described for formula (A), as if each and every combination is individually described.

PI3K Inhibitor Compounds

Provided herein are compounds that function as PI3K inhibitors. In one aspect, provided is a compound of formula (A), or a pharmaceutically acceptable salt, prodrug, or solvate wherein:

Formula (A)

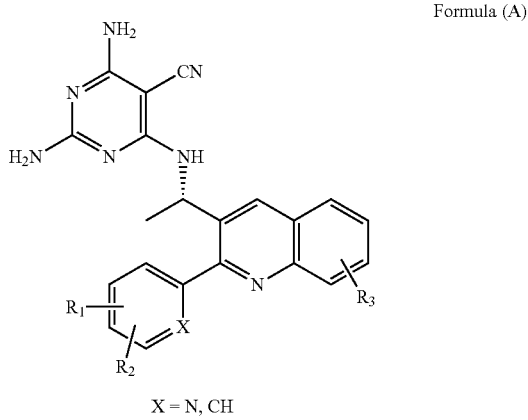

X = N, CH

X is N or CH;

Each $R_1$ and $R_2$ are independently H, F, or $SO_2Me$.

$R_3$ is F or Cl.

In one embodiment of formula (A) where X is N, both $R_1$ and $R_2$ are H, $R_3$ is 7-F. The compound is of compound (2) in Table 1; or a pharmaceutically acceptable salt, prodrug, or solvate thereof.

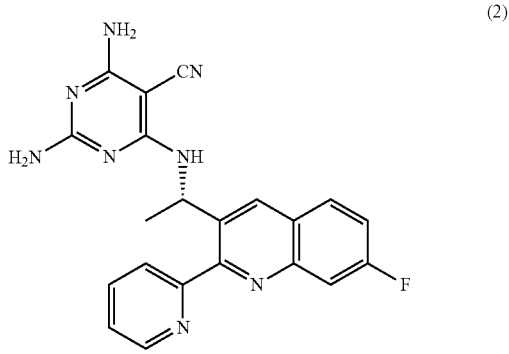 [SMILES: C[C@H](Nc1nc(N)nc(N)c1C#N)c1cc2ccc(F)cc2nc1-c1ccccn1]

(2)

In another embodiment of formula (A) where X is C, $R_1$ is H, $R_2$ is 2-$SO_2Me$, $R_3$ is 8-F, the compound is compound (7) in Table 1, or a pharmaceutically acceptable salt, prodrug, or solvate thereof.

(7)

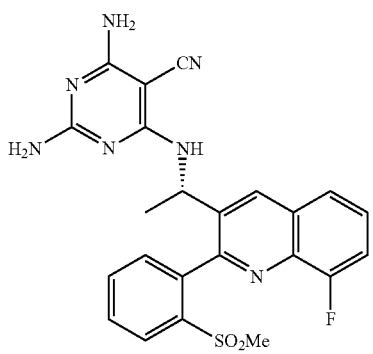

TABLE 1

Representative Quinoline Compounds of Formula (A)

| # | Structure | Name |
|---|---|---|
| 1 | | 2,4-Diamino-6-[1-(7-fluoro-2-phenyl-quinolin-3-yl)-ethylamino]-pyrimidine-5-carbonitrile |
| 2 | | 2,4-Diamino-6-[1-(7-fluoro-2-pyridin-2-yl-quinolin-3-yl)-ethylamino]-pyrimidine-5-carbonitrile |
| 3 | | 2,4-Diamino-6-{1-[2-(3,5-difluoro-phenyl)-7-fluoro-quinolin-3-yl]-ethylamino}-pyrimidine-5-carbonitrile |
| 4 | 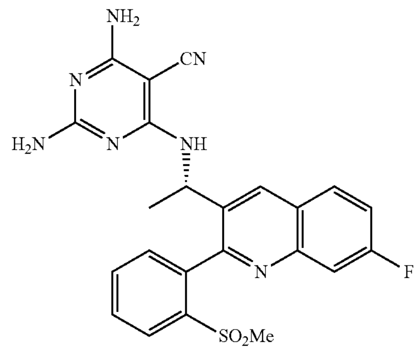 [SMILES: C[C@H](Nc1nc(N)nc(N)c1C#N)c1cc2ccc(F)cc2nc1-c1ccccc1S(C)(=O)=O] | 2,4-Diamino-6-{1-[7-fluoro-2-(2-methanesulfonyl-phenyl)-quinolin-3-yl]-ethylamino}-pyrimidine-5-carbonitrile |
| 5 | 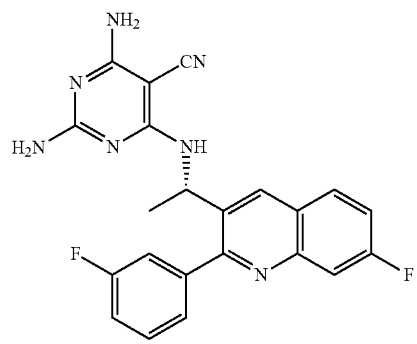 [SMILES: C[C@H](Nc1nc(N)nc(N)c1C#N)c1cc2ccc(F)cc2nc1-c1cccc(F)c1] | 2,4-Diamino-6-{1-[7-fluoro-2-(3-fluoro-phenyl)-quinolin-3-yl]-ethylamino}-pyrimidine-5-carbonilrile |
| 6 | 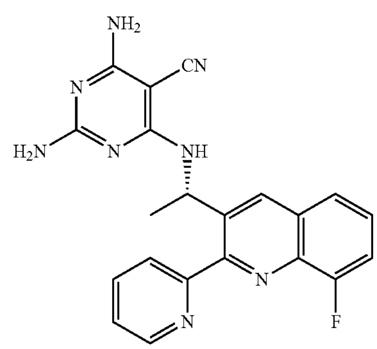 | 2,4-Diamino-6-[1-(8-fluoro-2-pyridin-2-yl-quinolin-3-yl)-ethylamino]-pyrimidine-5-carbonitrile |
| 7 | 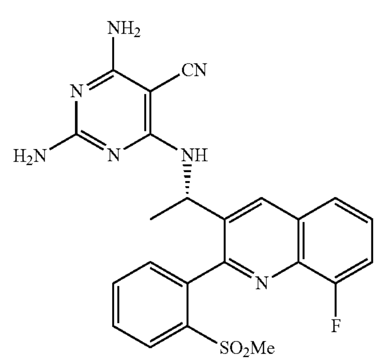 [SMILES: C[C@H](Nc1nc(N)nc(N)c1C#N)c1cc2cccc(F)c2nc1-c1ccccc1S(C)(=O)=O] | 2,4-Diamino-6-{1-[8-fluoro-2-(2-methanesulfonyl-phenyl)-quinolin-3-yl]-ethylamino}-pyrimidine-5-carbonitrile |

TABLE 1-continued

Representative Quinoline Compounds of Formula (A)

| # | Structure | Name |
|---|-----------|------|
| 8 | 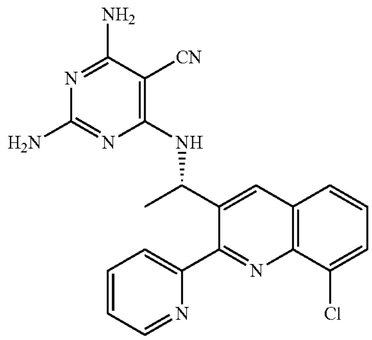 [SMILES: C[C@H](Nc1nc(N)nc(N)c1C#N)c1cc2cccc(Cl)c2nc1-c1ccccn1] | 2,4-Diamino-6-[1-(8-chloro-2-pyridin-2-yl-quinolin-3-yl)-ethylamino]-pyrimidine-5-carbonitrile |

Provided are also compounds of formula (A), or pharmaceutically acceptable salts, prodrugs, or solvates thereof. In certain embodiments, provided herein are also crystalline and amorphous forms of the compounds of formula (A), or pharmaceutically acceptable salt, prodrugs, or solvents thereof.

"Pharmaceutically-acceptable salt" means a salt prepared by conventional means, and are well known by those skilled in the art. The "pharmacologically acceptable salts" include basic salts of inorganic and organic acids (Berge et al., J. Pharm. Sci. 1977, 66:1).

A "solvate" is formed by treating a compound in a solvent. Solvates of salts of the compounds of formula (A) are also provided. In the case of treating compounds with water, the solvate is hydrates. Hydrates of the compounds of formula (A) are also provided.

A "prodrug" includes any compound that converts into a compound of formula (A), when administered to a subject, e.g., upon metabolic processing of the prodrug.

Therapeutic Uses of the Compounds

The compounds of formula (A), or pharmaceutically acceptable salt, prodrug, or solvate thereof may be used for treating PI3K mediated diseases or disorders. In one embodiment, provided are methods for inhibiting PI3K delta activity using a compound of formula (A), or a pharmaceutically acceptable salt, prodrug, or solvate thereof. In another embodiment, PI3K delta and gamma isomers may both be inhibited to achieve optimal efficacy.

In addition to the therapeutic uses described herein, selected compounds of formula (A), or a pharmaceutically acceptable salt, prodrug, or solvate thereof, have improved properties in at least one of the following parameters: (i) human hepatocyte stability, and (ii) pharmacokinetic profiles (PK) including oral exposure.

In another embodiment, selected compounds of formula (A), or a pharmaceutically acceptable salt, prodrug, or solvate thereof have improved human hepatocyte stability. Human hepatocyte stability in many cases correlates with pharmacokinetics in human better than the corresponding rodent pharmacokinetic studies. According to some embodiments, selected compounds may have hepatocyte stability of a half-life of greater than 24 hours.

As used herein, "treat" or "treating" in reference to a disorder means to ameliorate or prevent the disorder or one or more of the biological manifestations of the disorder, to interfere with one or more points in the biological cascade that leads to or is responsible for the disorder, to alleviate one or more of the symptoms or effects associated with the disorder. As indicated above, "treatment" of a disorder includes prevention of the disorder, and "prevention" is understood to refer to the prophylactic administration of a drug to substantially diminish the likelihood or severity of a disorder or biological manifestation thereof, or to delay the onset of such disorder or biological manifestation thereof.

"Subject" refers to a human (including adults and children) or other animal. In one embodiment, "patient" refers to a human.

As used herein, "safe and effective dose" in reference to a compound of formula (A), or a pharmaceutically acceptable salt, prodrug, or solvate thereof an amount sufficient to treat the patient's condition but low enough to avoid serious side effects. A safe and effective dose of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors.

"Inhibition of PI3K delta activity" or variants refer to a decrease in PI3K delta activity as a direct or indirect response to the presence of a compound of formula (A), or a pharmaceutically acceptable salt, prodrug, or solvate thereof, relative to the activity of PI3K delta in the absence of the compound of formula (A), or a pharmaceutically acceptable salt, prodrug, or solvate thereof.

The term "PI3K delta selective inhibitor" generally refers to a compound that inhibits the activity of the PI3K delta isoform more effectively than other isoforms of the PI3K family (e.g., PI3K alpha, beta, or gamma).

The potencies of compounds as inhibitors of an enzyme activity (or other biological activity) can be established by determining the concentrations at which each compound inhibits the activity to a predefined extent and then comparing the results. "IC50" or "IC90" of an inhibitor can be determined by the concentration that inhibits 50% or 90% of the activity in a biochemical assay, which can be accomplished using conventional techniques known in the art, including the techniques describes in the Examples below.

PI3K delta is expressed primarily in hematopoietic cells including leukocytes such as T-cells, dendritic cells, neutrophils, mast cells, B-cells, and macrophages. Due to its integral role in immune system function, PI3K delta is also involved in a number of diseases related to undesirable immune response such as allergic reactions, inflammatory diseases, inflammation mediated angiogenesis, rheumatoid arthritis, auto-immune diseases such as lupus, asthma, emphysema and other respiratory diseases. By inhibiting aberrant proliferation of hematopoietic cells, PI3K delta inhibitors can ameliorate the symptoms and secondary conditions that result from a primary effect such as excessive system or localized levels of leukocytes or lymphocytes.

In one aspect, the invention thus provides a method of treating a disorder mediated by inappropriate PI3-kinase activity comprising administering a safe and effective dose of a compound of formula (A), or a pharmaceutically acceptable salt, prodrug, or solvate thereof.

In one embodiment, PI3K mediated diseases or disorders are selected from the group consisting of respiratory diseases (including asthma, chronic obstructive pulmonary disease (COPD) and idiopathic pulmonary fibrosis (IPF)); allergic diseases (including allergic rhinitis and atopic dermatitis); autoimmune diseases (including rheumatoid arthritis and multiple sclerosis); inflammatory disorders (including inflammatory bowel disease); hematologic malignancies; solid tumors; neurodegenerative diseases; pancreatitis; kidney diseases; transplantation rejection; graft rejection; lung injuries In one embodiment, the compounds described herein may be used to treat cancers that are mediated by inappropriate PI3K delta activity. In certain embodiments, the disease is a hematologic malignancy. In certain embodiments, the disease is lymphoma, such as Burkitt lymphoma, diffuse large B-cell lymphoma (DLBCL) and mantle cell lymphoma (MCL), follicular lymphoma, lymphoplasmacytic lymphoma, Waldenstrom macroglobulinemia, and marginal zone lymphoma. In one embodiment, the disorder is multiple myeloma, or leukemia, such as acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML).

In other embodiments, the disease is a solid tumor. In particular embodiments, the indication is to treat solid tumor with abnormal PI3K delta expression, such as pancreatic cancer, gastric cancer, esophageal cancer, and breast cancer. In some embodiment, the compounds alone or with combination of other anti-cancer therapies may be used to treat prostate cancer, bladder cancer, colorectal cancer, renal cancer, hepatocellular cancer, lung cancer, ovarian cancer, cervical cancer, head and neck cancer, melanoma, neuroendocrine cancers, brain tumors, bone cancer, or soft tissue sarcoma.

In some embodiments, PI3K mediated diseases or disorders are severe autoimmune disease as asthma, type I diabetes, rheumatoid arthritis, multiple sclerosis, chronic obstructive pulmonary disease (COPD), and lupus.

Combination Therapies

In one embodiment, a compound of formula (A), or a pharmaceutically acceptable salt, prodrug, or solvate may be used in combination with one or more additional therapeutic agents to treat cancers or inflammatory disorders. The one or more additional therapeutic agents may be a chemotherapeutic agent, a radiotherapy, a targeted therapy, an immunotherapeutic agent or any current best of care treatment, either as a small molecule or a biologic nature.

Targeted therapies include but not limit to an inhibitor to cyclin-dependent kinase (CDK) such as CDK1, CDK2, CDK4/6, CDK7, and CDK9, Janus kinase (JAK) such as JAK1, JAK2 and/or JAK3, spleen tyrosine kinase (SYK), Bruton's tyrosine kinase (BTK), mitogen-activated protein kinase (MEK) such as MEK 1 and MEK2, bromodomain containing protein inhibitor (BRD) such as BRD4, isocitrate dehydrogenase (IDH) such as IDH1, histone deacetylase (HDAC), or any combination thereof.

Chemotherapeutic agents may be categorized by their mechanism of action into: alkylating agents, antimetabolites, anti-microtubule agents, topoisomerase inhibitors and cytotoxic agents. A compound of formula (A), or a pharmaceutically acceptable salt, prodrug, or solvate may be used in combination with chemotherapeutics to sensitize and improve the efficacy of certain chemotherapeutic agents to treat blood or solid tumors.

The immunotherapeutic agents include and are not limited to therapeutic antibodies, small molecules and vaccines suitable for treating patients; such as IDO1 and TDO2 inhibitors, A2A receptor inhibitors, arginase inhibitors, toll-like receptor agonists, chemokine regulators (including CCR and CXCR families), check point blockage antibodies such as antibodies that regulate PD-1, PD-L1, CTLA-4, OX40-OX40 ligand, LAGS, TIM3, or any combination thereof.

Radiotherapy is part of cancer treatment to control or kill malignant cells and commonly applied to the cancerous tumor because of its ability to control cell growth. A compound of formula (A), or a pharmaceutically acceptable salt, prodrug, or solvate may be used in combination with radiotherapy, to improve the efficacy of radiotherapy to treat blood or solid tumors, or with surgery, chemotherapy, immunotherapy and combination of the four.

In certain embodiments, a compound of formula (A), or a pharmaceutically acceptable salt, prodrug, or solvate may be used in combination with one or more additional therapeutic agents to treat patients who are substantially refractory to at least one chemotherapy treatment, or in relapse after treatment with chemotherapy.

Pharmaceutical Compositions

In another aspect, the present invention provides a pharmaceutical composition comprising a compound of formula (A), or a pharmaceutically acceptable salt, prodrug, or solvate salt thereof and a pharmaceutically acceptable carrier or excipient. The pharmaceutical composition can be formulated for particular routes of administration such as oral administration, parenteral administration, and topical administration, etc.

Compositions intended for oral use are prepared according to any method known in the art for the manufacture of pharmaceutical compositions and can be prepared in the form of tablets, pills, powders, suspensions, emulsions, solutions, syrups, and capsules. Oral composition may contain the active ingredient in admixture with nontoxic pharmaceutically acceptable excipients which are suitable for the manufacture of tablets. The tablets are uncoated or coated by known techniques to delay disintegration and absorption in the gastrointestinal tract and thereby provide a sustained action over a longer period. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or spray formulations, e. g., for delivery by aerosol or the like. Such topical delivery systems will in particular be appropriate for dermal application, e.g., for the treatment of skin cancer, e.g., for prophylactic use in sun creams, lotions, sprays and the like.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Modes of Administration and Dosing

The pharmaceutical compositions may be administered in either single or multiple doses. A compound of formula (A), or a pharmaceutically acceptable salt, prodrug, or solvate salt thereof can be formulated so as to provide the desired release schedule of the active ingredient based on the therapeutic treatment purpose.

The pharmaceutical composition is preferably made in the form of a dosage unit containing a particular amount of the active ingredient in the form of tablets, pills, powders, suspensions, emulsions, solutions, syrups, and capsules. For example, these may contain an amount of active ingredient from about 0.1 to 1000 mg, preferably from about 0.1 to 500 mg. A suitable daily dose for a human or other mammal may vary widely depending on the condition of the patient and other factors, but, once again, can be determined using routine methods. The daily dose can be administered in one to four doses per day. For therapeutic purposes, the active compounds of this invention are ordinarily combined with one or more adjuvants appropriate to the indicated route of administration drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g. from 1% to 2% by weight of the formulation, preferably not more than 5% w/w, and more preferably from 0.1% to 1% of the formulation.

In a particular embodiment, the method comprises administering to the subject an initial daily dose of about 0.1 to 500 mg of a compound of formula (A) and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds of Formula (A)

The compounds of formula (A) may be prepared using the methods disclosed herein and routine modifications thereof, which will be apparent given the disclosure herein and methods are well known in the art. Conventional and well-known synthetic methods may be used in addition to the teachings herein. The synthesis of representative compounds described herein may be accomplished as described in the following examples. If available, reagents may be purchased commercially, e.g., from Sigma Aldrich or other chemical suppliers.

General

Reagents and solvents used below can be obtained from commercial sources. 1H-NMR spectra were recorded on a Mercury 300 MHZ NMR spectrometer. Significant peaks are tabulated in the order: multiplicity (s, singlet; d, doublet; t, triplet; q, quartet; m, multiplet; br s, broad singlet), coupling constant(s) in Hertz (HZ) and number of protons. Mass spectrometry results are reported as the ratio of mass over charge, followed by the relative abundance of each ion (in parentheses Electrospray ionization (ESI) mass spectrometry analysis was conducted on an Agilent 1100 series LC/MSD electrospray mass spectrometer. All compounds could be analyzed in the positive ESI mode using acetonitrile water with 0.1% TFA as the delivery solvent.

Synthetic Reaction

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, dichloromethane (DCM), diethyl ether, methanol, pyridine and the like. Unless specified to the contrary, the solvents used in the reactions of the present invention are inert organic solvents, and the reactions are carried out under an inert gas, preferably nitrogen.

Preparation of 8-Substituted Quinoline Amines

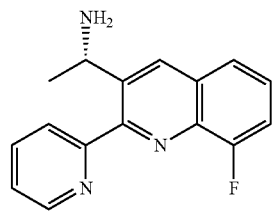

9

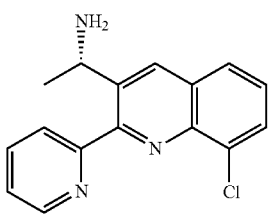

10

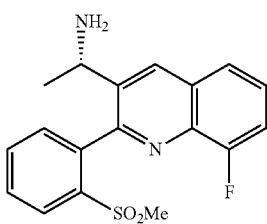

11

Example 1: (S)-1-(8-Fluoro-2-pyridin-2-yl-quinolin-3-yl)-ethylamine (9)

Step 1:

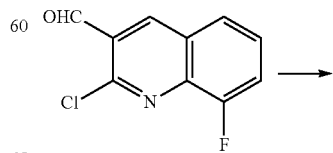

-continued

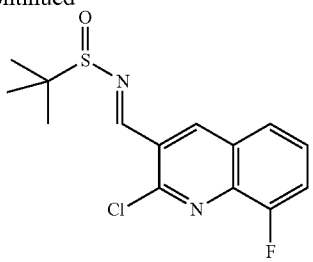

To a solution of 2-chloro-8-fluoroquinoline-3-carboxaldehyde (1.5 g, 7.2 mmol) in anhydrous THF (20 mL) was added titanium isopropoxide (4.3 mL, 1.4 mmol) at r.t. After 15 minutes, (R)-2-methyl-2-propanesulfinamide (0.867 g, 7.2 mmol) was added and stirring was continued overnight at r.t. Water (100 mL) was added to the reaction mixture and the precipitate obtained was filtered and washed with DCM. The organic layer was dried (Na2SO4), filtered and concentrated in vacuo to give the crude material as a pale yellow solid which was purified by column chromatography on silica gel (EtOAc/hexane, 4/5)) to give a pale yellow solid (2.0 g, 89%). Mass Spectrum (ESI) m/e: 313 (M+1).

Step 2:

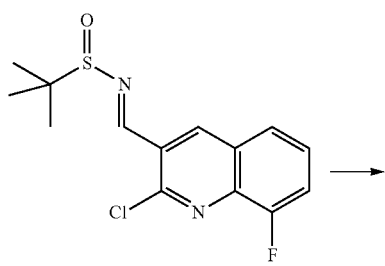

To a solution of 2-Methyl-propane-2-sulfinic acid 2-chloro-8-fluoro-quinolin-3-ylmethyleneamide (0.95 g, 2.8 mmol) in DCM (22 mL) was added dropwise MeMgCl (1.94 mL, 5.8 mmol; 3 M in THF) over 10 minutes at −78° C. under nitrogen. The reaction mixture was allowed to reach r.t. with stirring overnight. The mixture was cooled in ice-salt as saturated aqueous NH4Cl (50 mL) was slowly added with stirring. The aqueous layer was extracted with DCM (2×50 mL). The organic layer was dried (MgSO4) filtered and concentrated in vacuo to give a yellow oil which was purified by column chromatography on silica gel (EtOAc/hexane, 4/5 to EtOAc) to give a pale yellow solid (260 mg, 28%). Mass Spectrum (ESI) m/e: 329 (M+1).

Step 3:

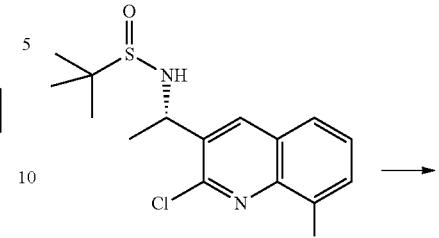

A mixture of (S)-2-Methyl-propane-2-sulfinic acid [1-(2-chloro-8-fluoro-quinolin-3-yl)-ethyl]-amide (0.186 g, 0.57 mmol), Pd(PPh3)4 (0.066 g, 0.057 mmol, 0.1 eq) and 2-(tributylstannyl)-pyridine (0.51 g, 1.4 mmol, 2.4 eq) in dioxane (5 mL) was heated to 110° C. under N2. After stirring overnight, the combined solvents were concentrated and purified by column chromatography on silica gel (EtOAc) to give 2-Methyl-propane-2-sulfinic acid [1-(8-fluoro-2-pyridin-2-yl-quinolin-3-yl)-ethyl]-amide (160 mg, 43%). Mass Spectrum (ESI) m/e: 372 (M+1).

To a solution of the above material (160 mg) in MeOH (2 mL) was added 4 N HCl in dioxane (2 mL) at rt and the resulted reaction mixture was stirred for 2 hours and concentrated under reduced pressure. Ethyl ether was added and sonicated for 2 min and filtered to give (S)-1-(8-fluoro-2-pyridin-2-yl-quinolin-3-yl)-ethylamine as HCl salt. Mass Spectrum (ESI) m/e: 268 (M+1).

(S)-1-(8-Chloro-2-pyridin-2-yl-quinolin-3-yl)-ethylamine (10) and (S)-1-[8-Fluoro-2-(2-methanesulfonyl-phenyl)-quinolin-3-yl]-ethylamine (11) were prepared in the similar manner.

Preparation of 7-Substituted Quinoline Amines

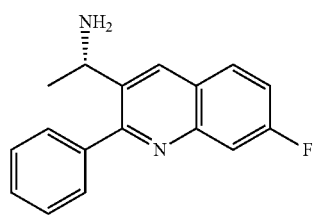

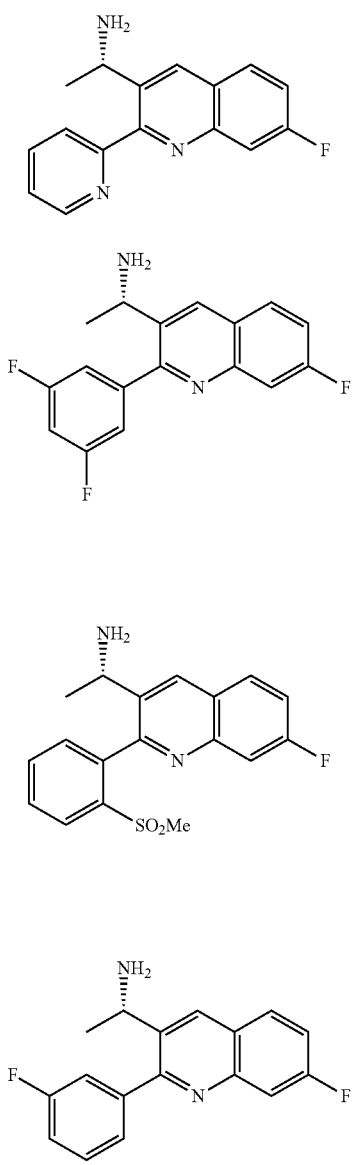

Example 2: (S)-1-(7-Fluoro-2-phenyl-quinolin-3-yl)-ethylamine (12)

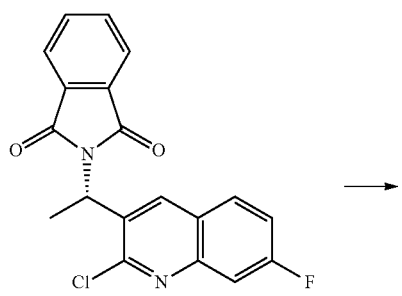

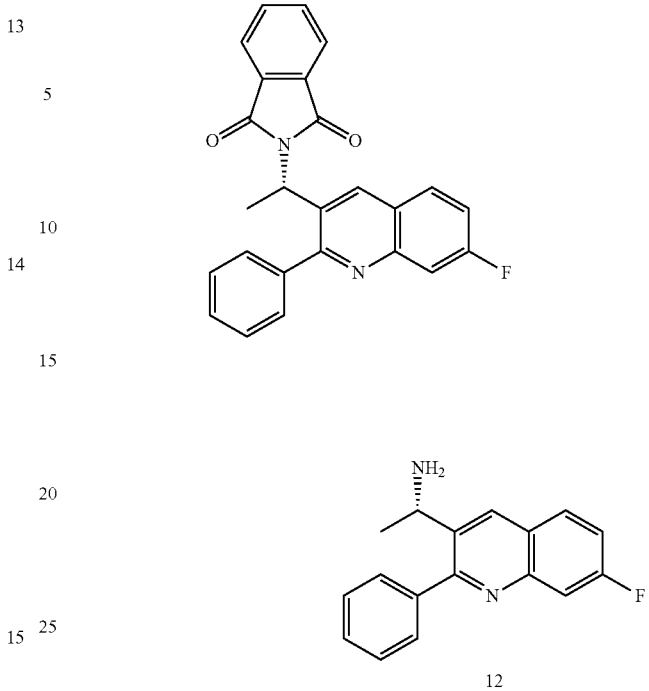

Compound (S)-2-(1-(2-Chloro-7-fluoroquinolin-3-yl)ethyl)isoindoline-1,3-dione was prepared according to the literature (J. Med. Chem. 2015, 58, 480-511). This compound (280 mg, 0.79 mmol), phenylboronic acid (146 mg, 1.2 mmol), and potassium carbonate (328 mg, 2.4 mmol) were combined in 6 mL of anhydrous DMF under an atmosphere of N2. The solution was purged with N2 for ~5 min before adding PdCl2(dppf)DCM (64 mg, 0.079 mmol). The solution was heated at 100° C. for 3 h, and then cooled to 50° C. The solution was concentrated under vacuum to give a brownish residue, which was diluted with EtOAc (12 mL). The organic layers were then washed with water (3×3 mL), followed by brine (10 mL). The combined aq. layers were extracted with DCM (3×2 mL). The combined organic layers were dried over MgSO4 and then concentrated under vacuum. The residue obtained was purified by silica gel flash chromatography eluting with a gradient of 20% to 40% EtOAc/hexane. The fractions containing the pure product were combined and concentrated under vacuum to give (S)-2-[1-(7-fluoro-2-phenyl-quinolin-3-yl)-ethyl]-isoindole-1,3-dione (263 mg, 84% yield) as a light yellow foam. Mass Spectrum (ESI) m/e: 397 (M+1).

To a slurried suspension of (S)-2-[1-(7-fluoro-2-phenyl-quinolin-3-yl)-ethyl]-isoindole-1,3-dione (260 mg, 0.65 mmol) in anhydrous ethanol (3 mL) was added NH2NH2 (0.11 g, 5.0 eq) dropwise. The reaction mixture was heated to 90° C. for 30 min and cooled to rt. The reaction mixture was filtered and washed with EtOAc. The resulting EtOAc solution was washed with water, brine and dried over Na2SO4. Removal of solvents gave a tan oil of (S)-1-(7-fluoro-2-phenyl-quinolin-3-yl)-ethylamine (122 mg, 71%). Mass Spectrum (ESI) m/e: 267 (M+1).

(S)-1-[2-(3,5-Difluoro-phenyl)-7-fluoro-quinolin-3-yl]-ethylamine (14), (S)-1-[7-Fluoro-2-(2-methanesulfonyl-phenyl)-quinolin-3-yl]-ethylamine (15), and (S)-1-[7-Fluoro-2-(3-fluoro-phenyl)-quinolin-3-yl]-ethylamine (16) were prepared in the similar manner.

Example 3: (S)-1-(7-fluoro-2-(pyridin-2-yl) quinolin-3-yl)ethanamine (13)

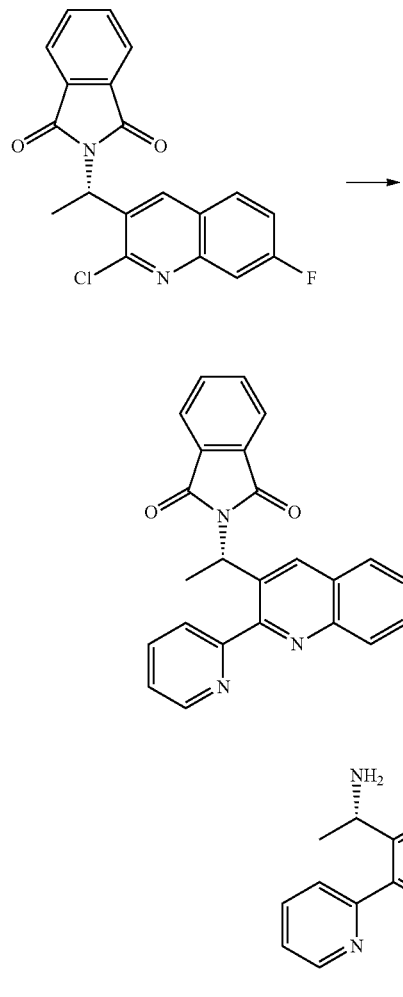

13

A mixture of (S)-2-(1-(2-chloro-7-fluoroquinolin-3-yl) ethyl)isoindoline-1,3-dione (0.86 g, 2.4 mmol), Pd(PPh3)4 (0.28 g, 0.24 mmol, 0.1 eq) and 2-(tributylstannyl)-pyridine (1.07 g, 2.9 mmol, 1.2 eq) in dioxane (30 mL) was heated to 90° C. under N2. After stirring overnight, LC-MS showed 30% completion. The reaction mixture was heated to 101° C. for additional 2 days. The reaction mixture was then cooled to rt and the resulted solid was filtered and washed with EtOAc to give a tan solid of 2-((S)-1-(7-fluoro-2 (pyridin-2-yl)quinolin-3-yl)ethyl)isoindoline-1,3-dione was obtained (0.84 g, 88%). Mass Spectrum (ESI) m/e: 398 (M+1).

To a slurried suspension of 2-((S)-1-(7-fluoro-2-(pyridin-2-yl)quinolin-3-yl)ethyl)isoindoline-1,3-dione (0.84 g, 2.1 mmol) in anhydrous ethanol (5 mL) was added NH2NH2 (0.34 g, 10.4 mmol) dropwise. The reaction mixture was heated to 90° C. for 30 min and cooled to rt. The reaction mixture was filtered and washed with EtOAc. The resulting EtOAc solution was washed with water, brine and dried over Na2SO4. Removal of solvents gave a tan oil of (S)-1-(7-fluoro-2-(pyridin-2-yl)quinolin-3-yl)ethanamine (399 mg, 71%). Mass Spectrum (ESI) m/e: 268 (M+1).

Preparation of 2,4,6-Triamino-pyrimidine-5-carbonitrile

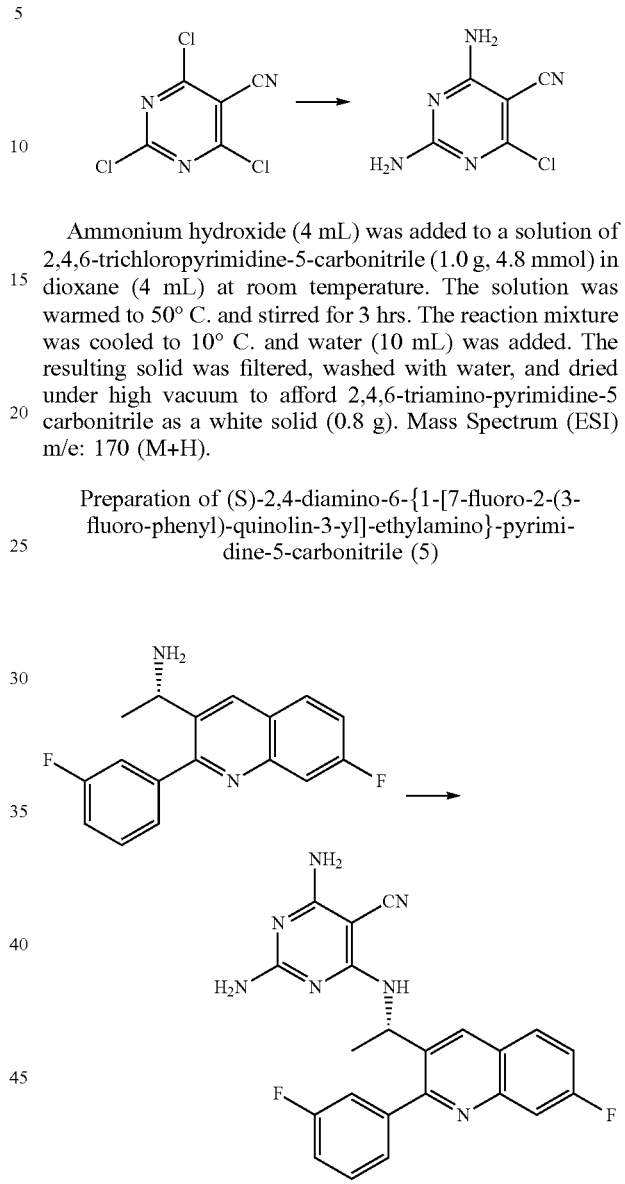

Ammonium hydroxide (4 mL) was added to a solution of 2,4,6-trichloropyrimidine-5-carbonitrile (1.0 g, 4.8 mmol) in dioxane (4 mL) at room temperature. The solution was warmed to 50° C. and stirred for 3 hrs. The reaction mixture was cooled to 10° C. and water (10 mL) was added. The resulting solid was filtered, washed with water, and dried under high vacuum to afford 2,4,6-triamino-pyrimidine-5 carbonitrile as a white solid (0.8 g). Mass Spectrum (ESI) m/e: 170 (M+H).

Preparation of (S)-2,4-diamino-6-{1-[7-fluoro-2-(3-fluoro-phenyl)-quinolin-3-yl]-ethylamino}-pyrimidine-5-carbonitrile (5)

Potassium fluoride (34 mg, 0.58 mmol) was added to a solution of (S)-1-[7-fluoro-2-(3-fluoro-phenyl)-quinolin-3-yl]-ethylamine (90 mg, 0.31 mmol) and 2,4-diamino-6-chloropyrimidine-5-carbonitrile (60 mg, 0.35 mmol) in diisopropylethylamine (0.1 mL, 0.60 mmol) and DMSO (2 mL). The resultant mixture was heated to 100° C. for 14 hours, after which time the reaction was cooled to room temperature, and diluted with water (5 mL) and the resulted solid was filtered, washed with water and dried and purified by preparative TLC to give a white solid as (S)-2,4-diamino-6-{1-[7-fluoro-2-(3-fluoro-phenyl)-quinolin-3-yl]-ethylamino}-pyrimidine-5-carbonitrile. Mass Spectrum (ESI) m/e: 418 (M+1). 1H NMR (300 MHz, DMSO-d6) δ ppm 8.49 (s, 1H), 8.10 (dd, J=5.7, 3.0 Hz, 1H), 7.75 (dd, J=11, 2.4 Hz, 1H), 7.52-7.60 (m, 3H), 7.27-7.32 (m, 1H), 7.12 (d, J=7.2 Hz, 1H), 6.52 (s, 2H), 6.10 (s, br, 2H), 5.40-5.45 (m, 1H), 1.30 (d, J=6.9 Hz, 3H).

The following compounds were prepared in the similar manner.

(S)-2,4-diamino-6-[1-(7-fluoro-2-phenyl-quinolin-3-yl)-ethylamino]-pyrimidine-5-carbonitrile (Compound 1, Table 1). Mass Spectrum (ESI) m/e: 400 (M+1). 1H NMR (300 MHz, DMSO-d6) δ ppm 8.46 (s, 1H), 8.07 (dd, J=6.6, 2.4 Hz, 1H), 7.67-7.70 (m, 2H), 7.49-7.52 (m, 3H), 7.13 (d, J=7.5 Hz, 1H), 6.52 (s, 2H), 6.10 (s, br, 2H), 5.45-5.50 (m, 1H), 1.27 (d, J=6.9 Hz, 3H).

(S)-2,4-Diamino-6-[1-(7-fluoro-2-pyridin-2-yl-quinolin-3-yl)-ethylamino]-pyrimidine-5-carbonitrile (Compound 2, Table 1). Mass Spectrum (ESI) m/e: 401 (M+1). 1H NMR (300 MHz, DMSO-d6) δ ppm 8.72 (s, 1H), 8.56 (m, 1H), 7.54-8.12 (m, 6H), 6.50 (s, 2H), 6.08 (s, br, 2H), 5.65-5.75 (m, 1H), 1.35 (d, J=6.9 Hz, 3H).

(S)-2,4-Diamino-6-{1-[2-(3,5-difluoro-phenyl)-7-fluoro-quinolin-3-yl]-ethylamino}-pyrimidine-5-carbonitrile (Compound 3, Table 1). Mass Spectrum (ESI) m/e: 436 (M+1). 1H NMR (300 MHz, DMSO-d6) δ ppm 8.52 (s, 1H), 8.13 (dd, J=5.7, 3.0 Hz, 1H), 7.76 (dd, J=7.5, 1.8 Hz, 1H), 7.54-7.60 (m, 1H), 7.08-7.45 (m, 2H), 7.09 (d, J=6.9 Hz, 1H), 6.52 (s, 2H), 6.12 (s, br, 2H), 5.35-5.40 (m, 1H), 1.34 (d, J=6.3 Hz, 3H).

(S)-2,4-Diamino-6-{1-[7-fluoro-2-(2-methanesulfonyl-phenyl)-quinolin-3-yl]-ethylamino}-pyrimidine-5-carbonitrile (Compound 4, Table 1). Mass Spectrum (ESI) m/e: 478 (M+1). 1H NMR (300 MHz, DMSO-d6) δ ppm 8.50 (s, 1H), 8.13 (dd, J=5.7, 3.0 Hz, 1H), 7.77-7.89 (m, 4H), 7.56-7.61 (m, 1H), 7.06 (d, J=7.5 Hz, 1H), 6.54 (s, 2H), 6.24 (s, br, 2H), 5.15-5.25 (m, 1H), 3.37 (s, 3H), 1.27 (d, J=6.9 Hz, 3H).

(S)-2,4-Diamino-6-[1-(8-fluoro-2-pyridin-2-yl-quinolin-3-yl)-ethylamino]-pyrimidine-5-carbonitrile (Compound 6, Table 1). Mass Spectrum (ESI) m/e: 401 (M+1). 1H NMR (300 MHz, DMSO-d6) δ ppm 8.51 (s, 1H), 8.16 (m, 1H), 7.54-8.02 (m, 6H), 6.51 (s, 2H), 6.01 (s, br, 2H), 5.23-5.34 (m, 1H), 1.30 (d, J=6.9 Hz, 3H).

(S)-2,4-Diamino-6-{1-[8-fluoro-2-(2-methanesulfonyl-phenyl)-quinolin-3-yl]-ethylamino}-pyrimidine-5-carbonitrile (Compound 7, Table 1). Mass Spectrum (ESI) m/e: 478 (M+1). 1H NMR (300 MHz, MeOH-d4) δ ppm 8.74 (d, J=4.5 Hz, 1H), 8.51 (s, 1H), 8.03-7.94 (m, 2H), 7.80 (d, J=8.4 Hz, 1H), 7.61-7.45 (m, 4H), 5.84 (q, J=6.9 Hz, 1H), 4.60 (s, 1H), 3.33 (s, 3H), 1.41 (d, J=6.9 Hz, 3H).

(S)-2,4-Diamino-6-[1-(8-chloro-2-pyridin-2-yl-quinolin-3-yl)-ethylamino]-pyrimidine-5-carbonitrile (Compound 8, Table 1). Mass Spectrum (ESI) m/e: 417 (M+1). 1H NMR (300 MHz, DMSO-d6) δ ppm 8.74 (d, J=4.5 Hz, 1H), 8.60 (s, 1H), 8.06-7.94 (m, 3H), 7.75 (d, J=8.4 Hz, 1H), 7.64-7.53 (m, 2H), 6.48 (s, 2H), 5.80-5.74 (m, 1H), 1.39 (d, J=6.0 Hz, 3H).

Biological Examples

Activity testing was conducted in the Examples below using methods described herein and those well known in the art.

Characterization of Compounds of Formula (A)

This Example compares the biological activity and hepatocyte stability of the compounds of formula (A) to 4-amino-2-hydrogen pyrimidine analogs D-F such as compounds having the following structure (Compounds D-F were reported in patent US2013/0267524 and compound D is a close analog for reference purpose).

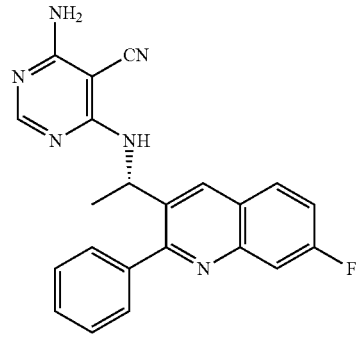

D

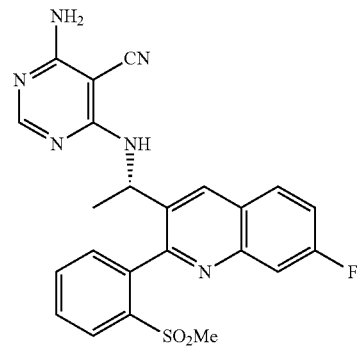

E

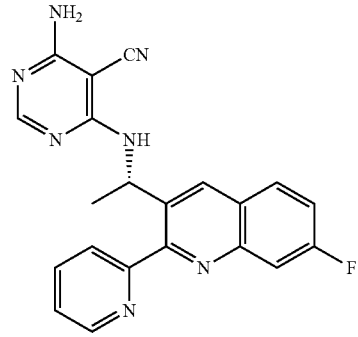 [SMILES: C[C@H](Nc1ncnc(N)c1C#N)c1cc2ccc(F)cc2nc1-c1ccccn1]

H

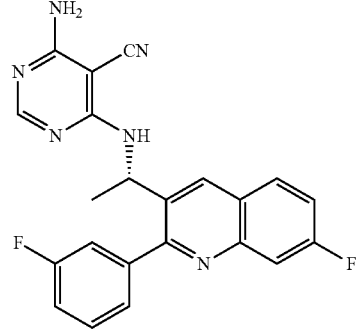 [SMILES: C[C@H](Nc1ncnc(N)c1C#N)c1cc2ccc(F)cc2nc1-c1cccc(F)c1]

G

-continued

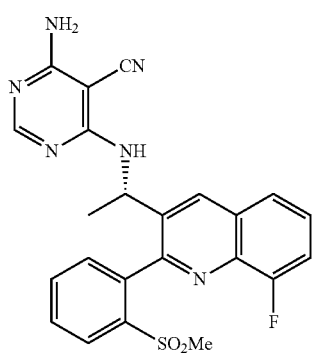

F

Enzymatic activity of different PI3K isoforms was measured to compare the PI3K isoform selectivity of the tested compounds, particularly selectivity of PI3K delta. Hepatocyte stability was also measured to assess the potential half-life of the tested compounds in human subjects.

Each of these biological experiments are described below.

Enzymatic Activity of PI3K Isoforms

Enzymatic activity of the class I PI3K isoforms in the presence of the compounds of Table 1 above was measured using a time-resolved fluorescence resonance energy transfer (TR-FRET) assay.

The TR-FRET assay can monitor formation of the product 3,4,5-inositol triphosphate molecule (PIP3) as it competed with fluorescently labeled PIP3 for binding to the GRP-1 pleckstrin homology domain protein. An increase in phosphatidylinositide 3-phosphate product results in a decrease in TR-FRET signal as the labeled fluorophore is displaced from the GRP-1 protein binding site.

The PI3K isoforms were assayed under initial rate conditions in the presence of 10 μM ATP, and compounds were tested in 10-dose IC50 mode starting at a concentration of 0.5 μM. Control compound, PI-103, was tested in 10-dose IC50 with 3-fold serial dilution starting at 10 μm.

Data are normalized based on negative (DMSO) control. The alpha, beta, delta, and gamma IC50 values were calculated from the fit of the dose-response curves to a four parameter equation. IC50 are reported in units of nM.

IC50 values were obtained for all PI3K isoforms (α, β, δ, and γ), and Table 2 summarizes the IC50 data collected for PI3Kδ in this Example.

Hepatocyte Stability

The hepatocyte assay was used to evaluate the metabolic stability of test articles (TA) following incubation in cryopreserved hepatocytes by monitoring parent drug disappearance via LC/MC. The TA with 1% final DMSO concentration was incubated with 0.5 million hepatocytes/ml at 1 μM substrate in duplicate. The incubation was carried out at 37° C. with 5% $CO_2$ and saturating humidity. Samples were taken at 0, 1, 2, and 3 hours to monitor the disappearance of TA and a half-life (t ½) was determined. Table 2 below summarizes the t½ values (e.g. t ½) collected from this Example.

TABLE 2

| Compound | $IC_{50}$ (nM) | hepatocyte $T_{1/2}$ (h) |
|---|---|---|
| 1 | 0.043 | 27 |
| 2 | 0.086 | 53 |
| 3 | 0.24 | 17 |
| 4 | 0.27 | 6 |
| 5 | 0.14 | 20 |
| 6 | — | 9 |
| 7 | 2.1 | 59 |
| 8 | 0.97 | — |
| D | — | 10 |
| E | — | 4.8 |
| H | — | 0.88 |
| G | — | 1.2 |
| F | — | 5.9 |

The results from this example demonstrate that compounds 1 and 4 of formula (A) have moderately improved stability in human hepatocytes (i.e. longer half-life), than compounds D and E (2.7× and 1.3×). However, several compounds showed surprisingly dramatic improvement for the stability in human hepatocytes (i.e. longer half-life); Table 3 below shows the comparison of t ½ of Compounds 2, 5, 7, H, G, and F. The dramatically improved stability of compounds in human hepatocytes will likely reduce the formation of drug metabolites in vivo and may contribute positively to the safety of the compounds in the clinical trials.

TABLE 3

| Compounds | 2 | 5 | 7 |
|---|---|---|---|
| T ½ (h) | >48 | >12 | >48 |
| Compounds | H | G | F |

TABLE 3-continued

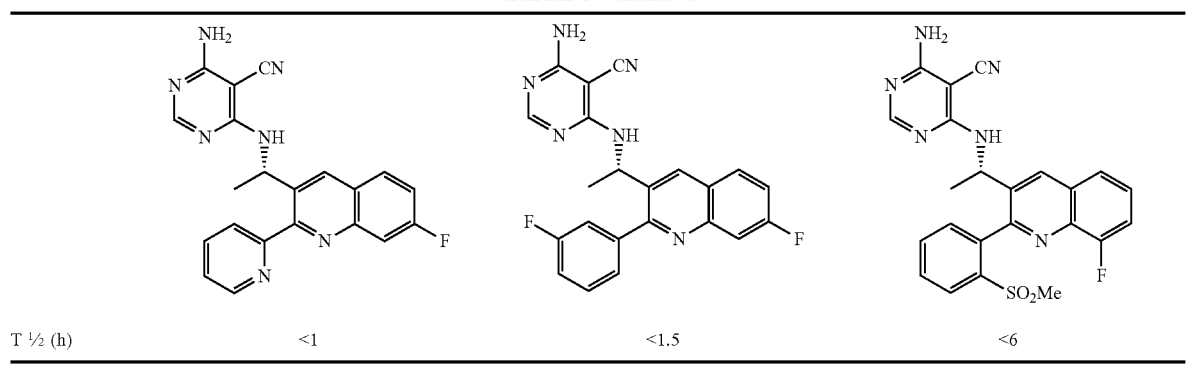

| T ½ (h) | <1 | <1.5 | <6 |

Compound 2 was dosed by both iv and PO in the rats. Shown in Table 4 is a comparison of PK profiles of 2 and marketed PI3K delta inhibitor idelalisib, also known as CAL-101 (PK data from idelalisib NDA filing): Compound 2 showed remarkably increased oral exposure after oral dose (10 mg/kg) in the SD rats. Oral exposure corrected with dose (AUCinf/dose) is 20 fold higher than that of idelalisib.

TABLE 4

| Test article | $AUC_{inf}$ (hr*ng/mL) | $AUC_{inf}$/Dose | $C_{max}$ (ng/mL) | $C_{max}$/Dose | $T_{max}$ (hr) | $t_{1/2}$ (hr) | $V_{SS}$ (L/kg) | Cl (ml/min/kg) | $F_\%$ |
|---|---|---|---|---|---|---|---|---|---|
| CAL-101 (IV) | 1151 ± 407 | 384 ± 136 | 1437 ± 220 | 479 ± 73 | 0.08 | 1.89 | 2.49 | 478 ± 19 | NA |
| CAL-101 (oral) | 422 ± 67 | 141 ± 22 | 129 ± 49 | 43 ± 16 | 3.00 | 1.52 | NA | NA | 39 ± 13 |
| Comp 2 (iv) | 4552 | 3448 | 1093 | 828 | 0.08 | 3.55 | 1.12 | 4.6 | |
| Comp 2 (po) | 29491 | 2949 | 3173 | 317 | 2 | 3.12 | 4.6 | 4.6 | 80 |

Cytotoxicity assay of compound 2 of Table 1 in selected cell lines

Procedure

Day 0: cell seeding for all cell lines with the density of 10000 cells/80 μL/well.

Day 1, drug treatment: Prepare 3-fold serial dilutions of compound stock solutions with growth medium. Dispense 20 μL (5×) drug solution in each well (duplicates for each concentration), the final DMSO concentration of each well treated with test compound and corresponding vehicle control is 0.1%. Incubate the plate for 72 h in specified incubator.

Day 4, plate reading: Thaw CTG solution and equilibrate to room temperature, add 100 μL of CTG per well, mix the contents for 2 min on the plate shaker, incubate for 10 min before recording the luminescence signal using Envision.

Data Analysis

The Cell viability (percent of control=T/C, the optical density of the test well after a 3-day period of exposure to test drug is T, and the control optical density is C) of each dose were fitted using a nonlinear regression model with a sigmoidal dose response with GraphPad Prism version 5, and the IC50 that the concentration of test drug where 100×T/C=50 were calculated

TABLE 5

| | $IC_{50}$ (μM) | | | | |
|---|---|---|---|---|---|
| Compound | EHEB | JVM-2 | SU-DHL-4 | SU-DHL-5 | SU-DHL-6 |
| Compound 2 | 0.216 | 0.931 | 0.088 | 0.493 | 0.035 |
| Idelalisib | 0.506 | 1.426 | 0.198 | 1.683 | 0.130 |
| Cisplatin | 2.592 | 0.749 | 0.507 | 0.280 | 5.606 |

What is claimed is:

1. A selective phosphoinositide 3-kinase delta (PI3δ) inhibitor compound having a structure of formula (A), or a pharmaceutically acceptable salt, or solvate thereof:

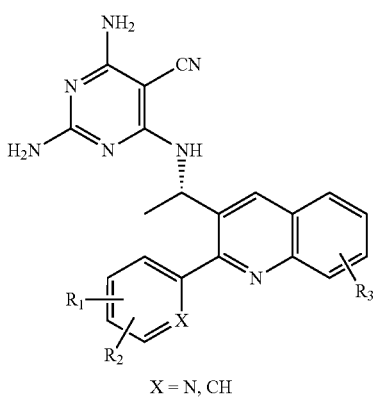

(A)

X = N, CH wherein X is N or CH;
$R_1$ and $R_2$ are each independently H, F, or $SO_2Me$, and $R_3$ is F or Cl.

2. The selective phosphoinositide 3-kinase delta (PI3Kδ) inhibitor compound of claim 1, wherein $R_3$ is 7-F, 8-F or 8-Cl, or a pharmaceutically acceptable salt, or solvate thereof.

3. The selective phosphoinositide 3-kinase delta (PI3Kδ) inhibitor compound of claim 2, wherein X is N, and each of $R_1$ and $R_2$ is H, or a pharmaceutically acceptable salt, or solvate thereof.

4. The selective phosphoinositide 3-kinase delta (PI3Kδ) inhibitor compound of claim 2, wherein X is CH and $R_1$ is $SO_2Me$, or a pharmaceutically acceptable salt, or solvate thereof.

5. The selective phosphoinositide 3-kinase delta (PI3Kδ) inhibitor compound of claim 2, wherein X is CH and $R_1$ is F, or a pharmaceutically acceptable salt, or solvate thereof.

6. The selective phosphoinositide 3-kinase delta (PI3Kδ) inhibitor compound of claim 2, wherein X is CH, $R_1$ is H and $R_2$ is H, or a pharmaceutically acceptable salt, or solvate thereof.

7. The selective phosphoinositide 3-kinase delta (PI3Kδ) inhibitor compound of claim 1, wherein X is N, each of $R_1$ and $R_2$ is H, and $R_3$ is 7-F, or a pharmaceutically acceptable salt, or solvate thereof.

8. The selective phosphoinositide 3-kinase delta (PI3Kδ) inhibitor compound of claim 1, wherein X is CH, $R_1$ is H, $R_2$ is 2-$SO_2Me$, and $R_3$ is 8-F, or a pharmaceutically acceptable salt, or solvate thereof.

9. The selective phosphoinositide 3-kinase delta (PI3Kδ) inhibitor compound of claim 1, wherein the compound's hepatocyte stability ranges from 6 to 59 $T_{1/2}$ (h), and wherein the compound has improved pharmacokinetics (PK) data than known PI3Kδ inhibitors.

10. A method of selectively inhibiting a growth or a proliferation phosphoinositide 3-kinase delta (PI3Kδ) comprising:
contacting kinase cells with an effective amount of a phosphoinositide 3-kinase delta (PI3Kδ) inhibitor compound having a structure of formula (A), or a pharmaceutically acceptable salt, or solvate thereof:

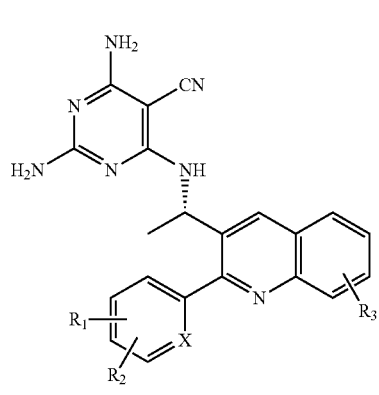

(A)

X = N, CH wherein X is N or CH;
$R_1$ and $R_2$ are each independently H, F, or $SO_2Me$, and $R_3$ is F or Cl.

11. The method of selectively inhibiting a growth or a proliferation phosphoinositide 3-kinase delta (PI3Kδ) according to claim 10, wherein $R_3$ is 7-F, 8-F or 8-Cl, or a pharmaceutically acceptable salt, or solvate thereof.

12. The method of selectively inhibiting a growth or a proliferation phosphoinositide 3-kinase delta (PI3Kδ) according to claim 10, wherein X is N, and each of $R_1$ and $R_2$ is H, or a pharmaceutically acceptable salt, or solvate thereof.

13. The method of selectively inhibiting a growth or a proliferation phosphoinositide 3-kinase delta (PI3Kδ) according to claim 10, wherein X is CH and $R_1$ is $SO_2Me$, or a pharmaceutically acceptable salt, or solvate thereof.

14. The method of selectively inhibiting a growth or a proliferation phosphoinositide 3-kinase delta (PI3Kδ) according to claim 10, wherein X is N, each of $R_1$ and $R_2$ is H, and $R_3$ is 7-F, or a pharmaceutically acceptable salt, or solvate thereof.

15. The method of selectively inhibiting a growth or a proliferation phosphoinositide 3-kinase delta (PI3Kδ) according to claim 10, wherein X is C, $R_1$ is H, $R_2$ is 2-$SO_2Me$, and $R_3$ is 8-F, or a pharmaceutically acceptable salt, or solvate thereof.

16. The method of selectively inhibiting a growth or a proliferation phosphoinositide 3-kinase delta (PI3Kδ) according to claim 10, wherein the compound has optimized hepatocyte stability varying from 6 to 59 $T_{1/2}$ (h), and wherein the compound has improved pharmacokinetics (PK) data than known PI3Kδ inhibitors.

17. A selective phosphoinositide 3-kinase delta (PI3Kδ) inhibitor compound having a structure of formula (A), or a pharmaceutically acceptable salt, or solvate thereof:

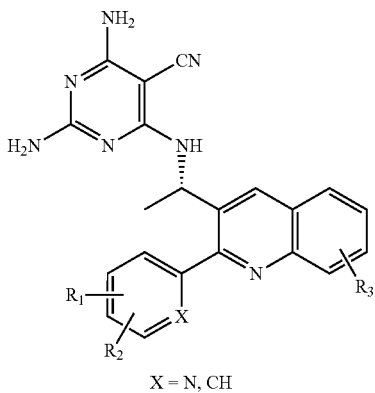

(A)

X = N, CH wherein X is N or CH;
$R_1$ is H;
$R_2$ is H or 2-$SO_2$Me, and
$R_3$ is 7-F or 8-F, wherein the compound has optimized hepatocyte stability varying from 6 to 59 $T_{1/2}$ (h).

18. The selective phosphoinositide 3-kinase delta (PI3Kδ) inhibitor compound of claim 17, wherein X is N, $R_2$ is H, and $R_3$ is 7-F, or a pharmaceutically acceptable salt, or solvate thereof.

19. The selective phosphoinositide 3-kinase delta (PI3Kδ) inhibitor compound of claim 17, wherein X is CH, $R_1$ is H, $R_2$ is 2-$SO_2$Me, and $R_3$ is 8-F, or a pharmaceutically acceptable salt, or solvate thereof.

20. The selective phosphoinositide 3-kinase delta (PI3Kδ) inhibitor compound of claim 17, wherein the compound has lowered cytotoxicity data than known PI3Kδ inhibitors, and wherein the compound has improved pharmacokinetics (PK) data than known PI3Kδ inhibitors.

* * * * *

UNITED STATES PATENT AND TRADEMARK OFFICE
CERTIFICATE OF CORRECTION

| | |
|---|---|
| PATENT NO. | : 10,792,283 B2 |
| APPLICATION NO. | : 16/072150 |
| DATED | : October 6, 2020 |
| INVENTOR(S) | : Hao |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 199 days.

Signed and Sealed this
Thirty-first Day of January, 2023

Katherine Kelly Vidal
*Director of the United States Patent and Trademark Office*